(12) United States Patent
Lee (10) Patent No.: US 10,665,080 B2
(45) Date of Patent: May 26, 2020

(54) METHODS AND SYSTEMS FOR BONE CONDUCTION AUDIBLE ALARMS FOR MECHANICAL CIRCULATORY SUPPORT SYSTEMS

(71) Applicant: TC1 LLC, St. Paul, MN (US)

(72) Inventor: Eric Lee, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 259 days.

(21) Appl. No.: 15/788,560

(22) Filed: Oct. 19, 2017

(65) Prior Publication Data

US 2018/0114426 A1    Apr. 26, 2018

Related U.S. Application Data

(60) Provisional application No. 62/410,670, filed on Oct. 20, 2016.

(51) Int. Cl.
| | |
|---|---|
| *G08B 21/04* | (2006.01) |
| *A61M 1/12* | (2006.01) |
| *H04R 25/00* | (2006.01) |
| *A61M 1/10* | (2006.01) |
| *G08B 3/10* | (2006.01) |

(52) U.S. Cl.
CPC ......... *G08B 21/0453* (2013.01); *A61M 1/101* (2013.01); *A61M 1/1001* (2014.02); *A61M 1/1086* (2013.01); *A61M 1/122* (2014.02); *G08B 3/10* (2013.01); *H04R 25/606* (2013.01); *A61M 2205/18* (2013.01); *H04R 2225/67* (2013.01); *H04R 2460/13* (2013.01)

(58) Field of Classification Search
None
See application file for complete search history.

(56) References Cited

U.S. PATENT DOCUMENTS

| | | |
|---|---|---|
| 5,695,471 A | 12/1997 | Wampler |
| 5,888,242 A | 3/1999 | Antaki et al. |
| 6,071,093 A | 6/2000 | Hart |

(Continued)

FOREIGN PATENT DOCUMENTS

| | | |
|---|---|---|
| EP | 1812094 B1 | 8/2011 |
| WO | 2016033118 A1 | 3/2016 |

OTHER PUBLICATIONS

Earlens Hearing Aid. [online]. Earlens.com, 1997 [retrieved on Aug. 15, 2016]. Retrieved from the Internet: <URL: (http://earlens.com/the-earlens-device/>.

*Primary Examiner* — Brian T Gedeon (74) *Attorney, Agent, or Firm* — Kilpatrick Townsend & Stockton LLP (57) ABSTRACT

A method for transmitting an alarm for a circulatory support system includes receiving an inaudible signal with a signal processor coupled to a hearing implant anchored in a bone behind a patient's ear. The inaudible signal is associated with an alarm of the system. A second alarm signal is transmitted along the bone to an inner ear of the patient based on the inaudible signal such that it is audibly perceived. A method for transmitting an alarm for a circulatory support system to a hearing implant anchored behind an ear of a patient includes receiving an inaudible signal with a signal processor that is coupled to the hearing implant. The inaudible signal is associated with an alarm of the system. A second alarm signal is transmitted to an inner ear of the patient based on the inaudible signal such that the second alarm signal is audibly perceived by the patient.

33 Claims, 8 Drawing Sheets

(56) References Cited

U.S. PATENT DOCUMENTS

| | | |
|---|---|---|
| 6,116,862 A | 9/2000 | Rau et al. |
| 6,186,665 B1 | 2/2001 | Maher et al. |
| 6,234,772 B1 | 5/2001 | Wampler et al. |
| 6,264,635 B1 | 7/2001 | Wampler et al. |
| 6,688,861 B2 | 2/2004 | Wampler |
| 6,991,595 B2 | 1/2006 | Burke et al. |
| 7,699,586 B2 | 4/2010 | Larose et al. |
| 7,976,271 B2 | 7/2011 | Larose et al. |
| 7,997,854 B2 | 8/2011 | Larose et al. |
| 8,007,254 B2 | 8/2011 | Larose et al. |
| 8,152,493 B2 | 4/2012 | Larose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | Larose et al. |
| 2002/0099412 A1 | 7/2002 | Fischell et al. |
| 2005/0071001 A1 | 3/2005 | Jarvik |
| 2007/0078293 A1 | 4/2007 | Shambaugh, Jr. et al. |
| 2008/0021394 A1 | 1/2008 | Larose et al. |
| 2008/0319544 A1 | 12/2008 | Yaegashi |
| 2009/0203957 A1 | 8/2009 | Larose et al. |
| 2010/0312040 A1 | 12/2010 | Puria et al. |
| 2012/0046514 A1 | 2/2012 | Bourque |
| 2012/0095281 A1 | 4/2012 | Reichenbach et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2015/0294550 A1 | 10/2015 | Kimball et al. |
| 2015/0350796 A1 | 12/2015 | Van |

METHODS AND SYSTEMS FOR BONE CONDUCTION AUDIBLE ALARMS FOR MECHANICAL CIRCULATORY SUPPORT SYSTEMS

CROSS-REFERENCES TO RELATED APPLICATIONS

This application claims the benefit of U.S. Provisional Application No. 62/410,670, filed Oct. 20, 2016, the entire contents of which are hereby incorporated by reference herein.

BACKGROUND

This application relates generally to mechanically assisted circulation systems, and more specifically relates to improved methods and systems for transmitting alarms for a mechanically assisted circulation system. Such alarms may be associated with an implantable blood pump, a power source, a controller or any other component of a mechanically assisted circulation system.

Mechanically assisted circulation systems, such as ventricular assist devices (VADs), often include an implantable blood pump and are used for both short-term (i.e., days, months, as a bridge to transplantation) and long-term applications (i.e., years or a lifetime, as a destination therapy) when a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a mechanically assisted circulation system while awaiting a heart transplant or as a long term destination therapy. A patient may also use a mechanically assisted circulation system while recovering from heart surgery. Thus, a mechanically assisted circulation system can supplement a weak heart (i.e., partial support) or can effectively replace the natural heart's function. Mechanically assisted circulation systems can be implanted in the patient's body and powered by an electrical power source inside or outside the patient's body. In some cases, patients may wear or otherwise carry peripherals (often referred to as controllers) that can serve as a patient interface and can perform multiple functions such as mechanically assisted circulation system control, power handling, diagnostics, data collection and troubleshooting.

In view of the life sustaining nature of the support provided by a mechanically assisted circulation system, close monitoring of the mechanically assisted circulation system is important to detect faults within the mechanically assisted circulation system that, if not suitably addressed in time, may result in failure of the mechanically assisted circulation system that may endanger the life of the patient. In order to ensure that detected faults are addressed in time, a patient is typically notified through a combination of audible, visual, and haptic feedback, often provided by peripherals as described above. Because visual and haptic feedback can be easily obscured or blocked by clothing, placement, or physical separation of the device from the body, audible alarms are often the most effective type of feedback to ensure a patient is alerted of the fault. However, audible alarms can be challenging to discern by a patient under some conditions. For example, if a patient has diminished hearing or is in a loud ambient environment, an audible alert may not be easily detected by a patient. Moreover, in quiet public settings, loud audible alerts may not be desirable to the patient, as they may draw unwanted attention.

Accordingly, improved methods, systems, and devices for alarm transmission are desirable for mechanically assisted circulation systems.

BRIEF SUMMARY

Improved methods and systems for transmitting alarms of circulatory support systems are provided. For example, inaudible signals associated with such alarms are received by a signal processor coupled to a hearing implant worn by a patient, and select alarm signals based on the inaudible signals are transmitted to an inner ear of the patient via bone conduction or other pathways that improve the ability of the patient to easily discern the alarm without interrupting others and/or in loud ambient environments.

Thus, in one aspect, a method is provided of transmitting an alarm for a circulatory support system of a patient. The method includes receiving a first inaudible signal from the circulatory support system of the patient with a sound processor that is operatively coupled to an implant anchored in a bone behind an ear of the patient, the first inaudible signal associated with an alarm of the circulatory support system. The method further includes transmitting a second alarm signal along the bone of the patient to an inner ear of the patient based on the first signal such that the second alarm signal is audibly perceived by the patient.

In many embodiments of the method, vibrations or sound waves are conducted along the bone of the patient. In some embodiments of the method, transmitting the second alarm signal includes transmitting vibrations or sound waves that are conducted along the bone of the patient such that the vibrations or sound waves are only audibly perceived by the patient when conducted along the bone of the patient. Transmitting the second alarm signal may include generating vibrations or sound waves that are conducted along the bone of the patient to an auditory portion of a cochlea of the inner ear of the patient.

In many embodiments of the method, the first inaudible signal is associated with an advisory alarm or a hazard alarm of the circulatory support system. The advisory alarm can be associated with at least one of a disconnected power cable, a low voltage of a power source of the circulatory support system, a low speed of the circulatory support system, a fault of a controller of the circulatory support system, or a fault of a backup power source of the circulatory support system. The hazard alarm can be associated with at least one of a stopped circulatory support system, a disconnected driveline of the circulatory support system, multiple disconnected power cables, an excessively low speed of the circulatory support system, or an excessively low voltage of the power source of the circulatory support system.

In some embodiments of the method, the type of the alarm may be used to determine aspects of the second alarm signal. For example, the method may further include processing the first inaudible signal to determine if the second alarm signal should be transmitted, wherein the second alarm signal is transmitted only when the first inaudible signal is associated with the hazard alarm of the circulatory support system. In some embodiments of the method, at least one parameter of the second alarm signal is determined based on whether the first inaudible signal is associated with the advisory alarm or the hazard alarm. For example, at least one of a frequency, intensity, or duration of the second alarm signal may be determined based on whether the first inaudible signal is associated with the advisory alarm or the hazard alarm. This may ensure that more serious alarms are noticed by the patient or caregiver. In many embodiments, the method further includes receiving wake up signals. For example, the method may further include receiving a wake up signal from a controller coupled to the circulatory support system prior to receiving the first inaudible signal. This may preserve battery power since a component may not need to be powered on when not receiving alarm signals, which may allow for a longer battery life and less need to charge the component.

In many embodiments of the method, the implant is anchored in the bone behind the ear to expose an abutment of the implant. The abutment is configured to facilitate releasable coupling of the sound processor to the implant. In some embodiments, the sound processor includes a rechargeable battery for powering the sound processor. This may allow easy replacement and charging of the sound processor to ensure that patients with mechanically assisted circulation systems can adequately hear alarms associated with the systems.

The circulatory support system includes an implantable blood pump and a controller communicatively coupled to the implantable blood pump. In some embodiments, the controller includes an external controller communicatively coupled to the implantable blood pump and configured to receive the first inaudible signal from the external controller with the sound processor from outside the body. In other embodiments, the controller includes an implantable controller communicatively coupled to the implantable blood pump and configured to receive the first inaudible signal from the implantable controller with the sound processor from within the body. In some embodiments of the method, receiving the first signal includes wirelessly receiving the first signal from the controller with the sound processor. In other embodiments of the method, receiving the first signal includes receiving the first signal from the controller with the sound processor via a hard wired connection between the controller and the sound processor. Wireless transmission may be beneficial in that it avoids cumbersome wires between components and allows flexibility in the placement of components. Moreover, wireless transmission may allow communication with both fully implanted and partially implanted mechanically assisted circulation systems.

In many embodiments of the method, audible signals may also be transmitted. In some embodiments of the method, the first inaudible signal is received by the sound processor from a controller of the circulatory support system, and the controller is configured to emit an audible signal associated with the alarm of the circulatory support system simultaneously with the transmission of the first inaudible signal to the sound processor. This may provide further assurances that the patient or another person in the vicinity may be alerted to the alarm, particularly in the case of a serious hazard alarm. In some embodiments, the method further includes transmitting a third signal associated with the alarm based on the first inaudible signal, wherein the third signal is an audible signal.

In another aspect, a method is provided of transmitting an alarm for a circulatory support system of a patient to a hearing implant anchored behind an ear of the patient. The method includes receiving a first inaudible signal from the circulatory support system of the patient with a signal processor that is operatively coupled to the hearing implant anchored behind the ear of the patient, the first inaudible signal associated with an alarm of the circulatory support system. The method further includes transmitting a second alarm signal to an inner ear of the patient based on the first inaudible signal such that the second alarm signal is audibly perceived by the patient.

In many embodiments of the method, the signal processor includes a sound processor. For example, transmitting the second alarm signal to the inner ear may include generating vibrations or sound waves that are conducted from at least one of a tooth or a bone of the patient to an auditory portion of a cochlea of the inner ear of the patient. It will be appreciated however that the signal processor is not limited to a sound processor, and in many embodiments may also include a photon processor. For example, transmitting the second alarm signal to the inner ear may include transmitting, with the photon processor, a photonic signal based on the first inaudible signal to a lens resting on the eardrum of the patient, and generating, with an actuator coupled to the lens, vibrations or sound waves based on the photonic signal that are conducted from the eardrum of the patient to the inner ear of the patient.

In yet another aspect, a mechanical circulatory support system is provided. The mechanical circulatory support system includes an implantable blood pump and a controller communicatively coupled to the implantable blood pump. The system further includes a sound processor configured to receive a first inaudible signal from the controller associated with an alarm of the circulatory support system and to generate a second alarm signal based on the first inaudible signal. The system further includes a bone conductor implant configured to be anchored into a bone behind an ear of a patient and operatively coupled to the sound processor, the bone conductor implant configured to transmit the second alarm signal along the bone of the patient to an inner ear such that the second alarm signal is audibly perceived by the patient.

In many embodiments of the system, audible signals are also emitted. In some embodiments of the system, the controller is configured to emit an audible signal associated with the alarm of the circulatory support system simultaneously with the transmission of the first inaudible signal to the sound processor. For example, the audible signal emitted from the controller is configured to be mutable based on a type of the alarm. As a further example, the audible signal emitted from the controller is configured to be mutable when the type of the alarm is an advisory alarm, wherein the advisory alarm includes at least one of a disconnected power cable, a low voltage of a power source of the circulatory support system, a low speed of the circulatory support system, a fault of a controller of the circulatory support system, or a fault of a backup power source of the circulatory support system.

It will be appreciated that the system may be used with a variety of controllers. In many embodiments of the system, the controller is implantable in the patient's body. In other embodiments of the system, the controller is an external controller.

In many embodiments of the system, the second alarm signal includes vibrations or sound waves that are conducted along the bone such that the vibrations or sound waves are only audibly perceived by the patient when conducted along the bone of the patient. In some embodiments of the system, the sound processor is further configured to transmit a third signal associated with the alarm based on the first inaudible signal, wherein the third signal is an audible signal. For example, the sound processor may be configured to transmit the third audible signal based on a type of the alarm. As a further example, the sound processor may be configured to transmit the third audible signal when the type of the alarm is a hazard alarm, wherein the hazard alarm includes at least one of a stopped circulatory support system, a disconnected driveline of the circulatory support system, multiple disconnected power cables, an excessively low speed of the circulatory support system, or an excessively low voltage of the power source of the circulatory support system.

In many embodiments of the system, the sound processor is configured to be activated upon receipt of a wake up signal from the controller prior to receiving the first inaudible signal. In some embodiments of the system, the sound processor is releasably coupled to the bone conductor implant via an exposed abutment. In many embodiments, the sound processor comprises a rechargeable battery configured to power the sound processor.

The above brief summary presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

For a fuller understanding of the nature and advantages of the present invention, reference should be made to the ensuing detailed description and accompanying drawings.

DETAILED DESCRIPTION

Aspects of the present disclosure relate to improved methods and systems for alarm transmissions, particularly in relation to mechanical circulatory support systems. For example, patients who have diminished hearing can now easily discern alarms emitted from their mechanical circulatory support system. In particular, the present invention provides for a signal processor coupled to a hearing implant worn by a patient which is configured to transmit select alarm signals based on inaudible alarm signals emitted from the mechanical support system to an inner ear of the patient via bone conduction or other pathways that improve the ability of the patient to audibly perceive the alarm. This invention further allows for effective alarm transmission in loud ambient environments and even in quiet environments without alerting others of the alarm transmission.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
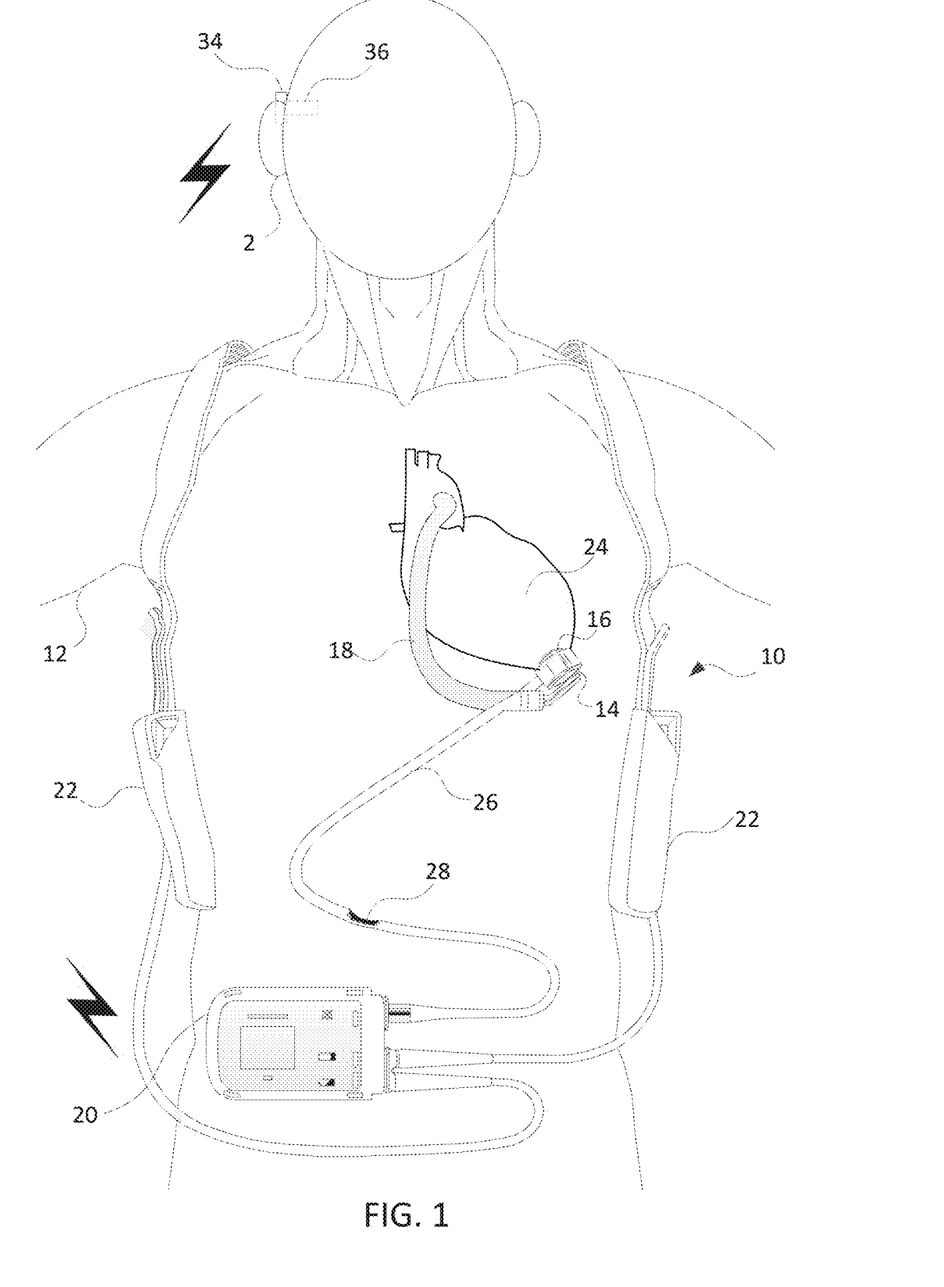
FIG. 1 is an illustration of a mechanical circulatory support system implanted in a patient's body, in accordance with many embodiments.

Referring now to the drawings, in which like reference numerals represent like parts throughout the several views, FIG. 1 shows an illustration of a mechanical circulatory support system 10 implanted in a patient's body 12. The mechanical circulatory support system 10 includes an implantable blood pump assembly 14, ventricular cuff 16, outflow cannula 18, an external system controller 20, and power sources 22. The implantable blood pump assembly 14 can include a VAD that is attached to an apex of the left ventricle, as illustrated, or the right ventricle, or both ventricles of the heart 24. The VAD can include a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 1, the blood pump assembly 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 that exits through the patient's abdomen 28, connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump assembly 14. Examples of such modifications are further described in U.S. Pat. No. 8,562,508 and U.S. Patent Publication No. 2013/0127253, all of which are incorporated herein by reference for all purposes in their entirety.

Figure 2:
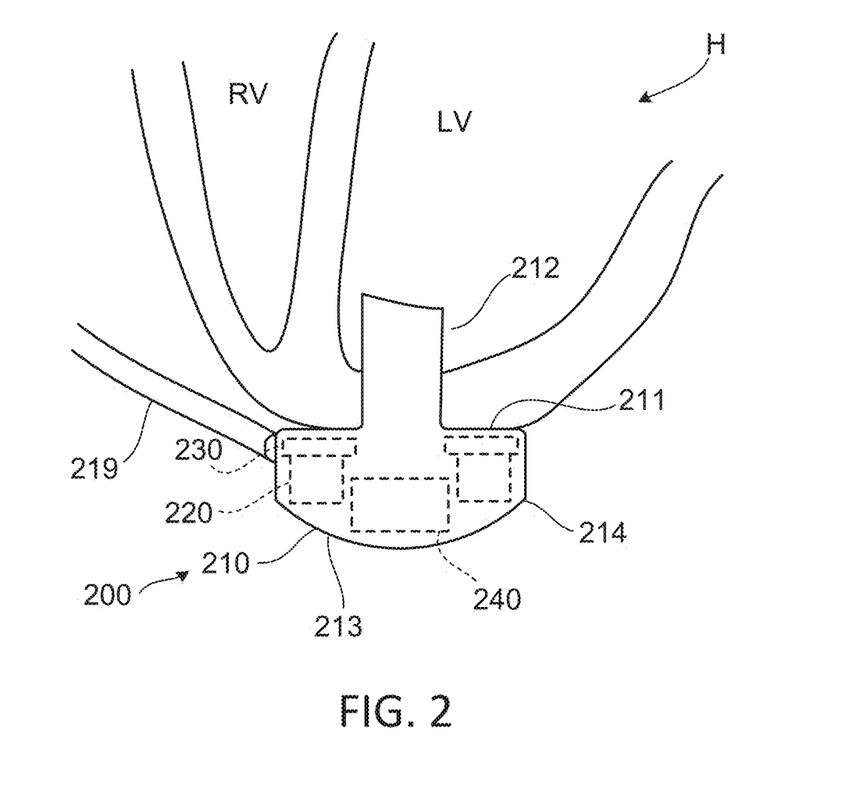
FIG. 2 is an illustration of a blood pump in an operational position implanted in a patient's body, in accordance with many embodiments.

With reference to FIG. 2, a left ventricular assist blood pump assembly 200 (which may correspond with blood pump assembly 14 described above) having a circular shaped housing 210 is implanted in a patient's body with a first face 211 of the housing 210 positioned against the patient's heart H and a second face 213 of the housing 210 facing away from the heart H. The first face 211 of the housing 210 includes an inlet cannula 212 extending into the left ventricle LV of the heart H. The second face 213 of the housing 210 has a chamfered edge 214 to avoid irritating other tissue that may come into contact with the blood pump assembly 200, such as the patient's diaphragm. To construct the illustrated shape of the puck-shaped housing 210 in a compact form, a stator 220 and electronics 230 of the pump assembly 200 are positioned on the inflow side of the housing toward first face 211, and a rotor 240 of the pump assembly 200 is positioned along the second face 213. This positioning of the stator 220, electronics 230, and rotor 240 permits the edge 214 to be chamfered along the contour of the rotor 240, as illustrated in FIG. 2, for example.

Figure 3:
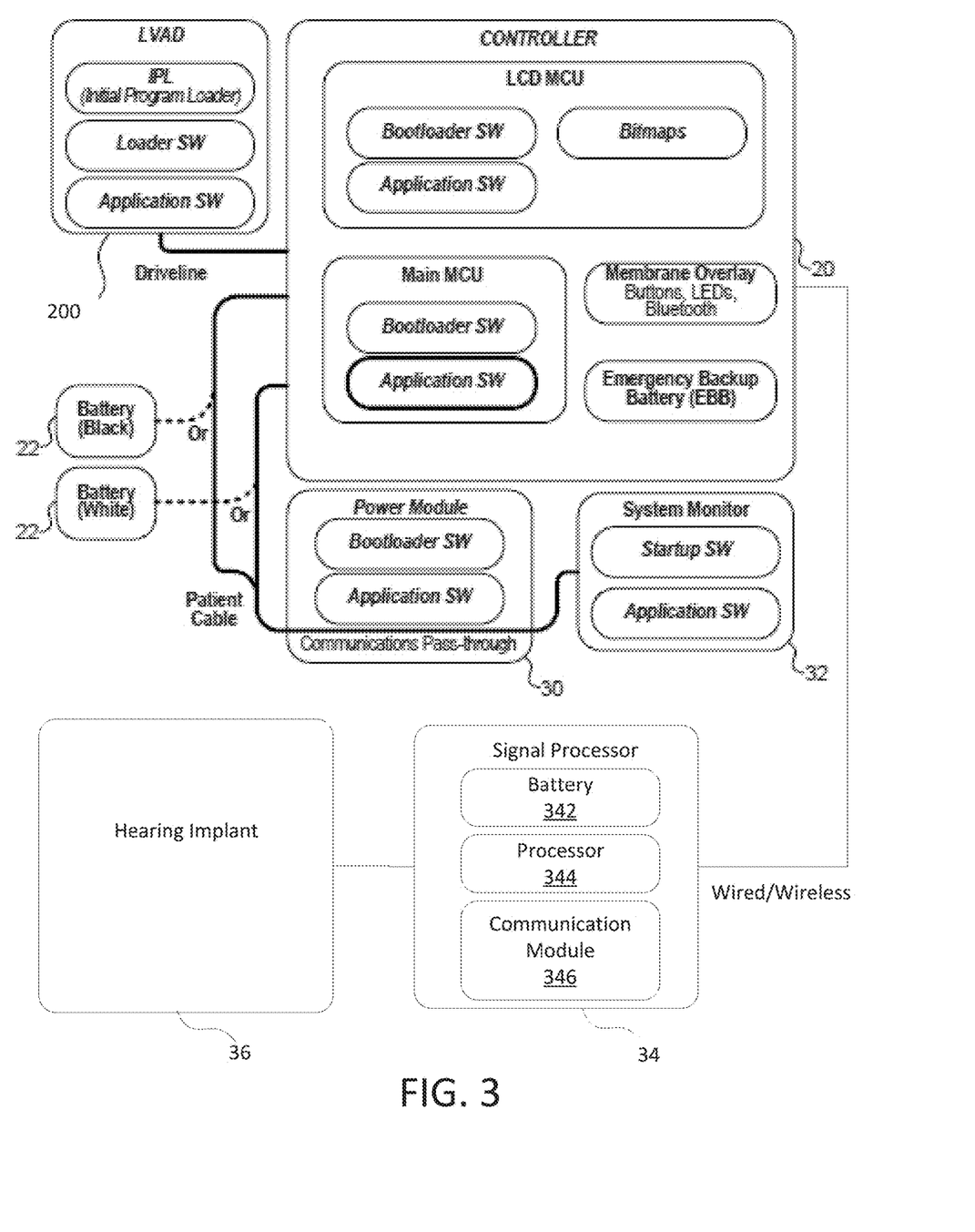
FIG. 3 is a schematic diagram of an overall communication architecture of the mechanical support system of FIG. 1, in accordance with many embodiments.

FIG. 3 is a schematic diagram of an overall communication architecture of the mechanical support system of FIG. 1. A driveline couples the implanted blood pump assembly 200 to the external system controller 20, which monitors system operation via various software applications. The blood pump assembly 200 itself also includes several software applications that are executable by the on board electronics 230 (e.g., processors) for various functions, such as to control radial levitation and/or drive of the rotor of the pump assembly 200 during operation. The external system controller 20 may in turn be coupled to either batteries 22 or a power module 30 that connects to an AC electrical outlet. The external system controller 20 may also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the external system controller 20, implanted blood pump assembly 200, and/or patient specific parameters, updating software on the external system controller 20 and/or implanted blood pump assembly 200, monitoring system operation, and/or as a conduit for system inputs or outputs.

As described above, due to the critical nature of mechanical circulatory support systems, close monitoring of mechanical circulatory support systems such as those described above with respect to FIGS. 1-3 may be used to detect faults within the mechanical circulatory support system and outputting alarms based thereon. Examples of such monitoring and alarming are further described in U.S. Patent Publication No. 2015/0294550, the contents of which are incorporated herein by reference for all purposes in their entirety. The alarms may include advisory alarms associated with a disconnected power cable, a low voltage of a power source of the circulatory support system, a low speed of the circulatory support system, a fault of a controller of the circulatory support system, or a fault of a backup power source of the circulatory support system and more critical hazard alarms associated with a stopped circulatory support system, a disconnected driveline of the circulatory support system, multiple disconnected power cables, an excessively low speed of the circulatory support system, or an excessively low voltage of the power source of the circulatory support system. In many embodiments, advisory and hazard alarms may be communicated to the patient using visible, audible, and haptic feedback. For example, controllers may detect one of the above faults and send a combination of visible, audible, and haptic feedback to the patient so that the faults can be addressed. While audible alarms are typically the most effective in alerting patients, typical audible alarms such as tones emitted by a peripheral such as a controller may not be easily discerned in loud ambient environments and/or by patients with hearing difficulties, and they may be disruptive in certain public settings. Improved methods and systems for transmitting alarms for a circulatory support system are thus described with reference to FIGS. 1-9.

Turning back to FIG. 1, system 10 may further include a signal processor 34 coupled to a hearing implant 36 for improved alarm transmission. As shown in FIG. 1, hearing implant 36 may be anchored behind the ear 2 of the patient 12, and signal processor 34 may be coupled directly to hearing implant 36. In some embodiments, hearing implant 36 may be anchored to a bone of a patient, as will be described in further detail with reference to FIGS. 4A-4B and 5.

As shown in FIG. 3, signal processor 34 may be configured to communicate with controller 20. Signal processor 34 may communicate through a wired connection or a wireless connection. For example, signal processor 34 may have a communication module 346 that includes a wireless transmitter and/or receiver to receive signals wirelessly from controller 20. Signal processor 34 and controller 20 may be configured to communicate via any suitable wireless communication protocol, including Bluetooth, Bluetooth Low Energy (BLE), WiFi, and any suitable combination thereof. For example, signal processor 34 and controller 20 may be paired together by BLE and may exchange signals wirelessly using this BLE connection. In some embodiments, if controller 20 is implanted within the body, signal processor 34 and controller 20 may be configured to communicate via the Medical Device Radiocommunications Service (MedRadio) and/or the Medical Implant Communication Service (MICS) protocols. In some embodiments, signal processor 34 and controller 20 may communicate with one another using industrial, scientific and medical (ISM) radio bands.

As shown in FIG. 3, signal processor may include a battery 342, a processor 344, and the aforementioned communication module 346. In some embodiments, battery 342 may be configured to power signal processor and the components thereof. Battery 342 may be a rechargeable battery. For example, signal processor may be able to connect to an external power source to recharge battery 342 during use and/or when not in use. Battery 342 may be replaceable. For example, battery 342 may be easily removable by the patient when necessary to recharge or replace the battery.

Processor 344 may perform any suitable signal processing as will be described below, including processing of any signals received from controller 20 and/or processing of any signals to be output by signal processor 34 to hearing implant 36. In many embodiments, processor 344 may be configured to generate and transmit vibrations or sound waves to hearing implant 36 based on signals received from controller 20. In some embodiments, processor 344 may include a photonic processor configured to generate and transmit photonic signals, as will be described in further detail with reference to FIG. 6 below. Processor 344 may be configured to generate audible tones in addition to the vibrations and/or photonic signals described above. For example, processor 344 may generate tones that can be output by speakers disposed on signal processor 34.

With further reference to FIG. 3, signal processor 34 may be configured to communicate with hearing implant 36. As described above, signal processor 34 may be directly coupled to hearing implant 36, which coupling may include an electrical connection through which signal processor 34 may transmit signals to hearing implant 36. It will be appreciated that signal processor 34 and hearing implant 36 may be configured to communicate wirelessly using any of the communication methods described above.

Although it will be understood that controller 20 may be configured to detect faults of system 10 and transmit visible, audio, and/or haptic alarms to alert patients of any of the alarms discussed above, including advisory and hazard alarms, in many embodiments, controller 20 may also be configured to transmit alarms to patient 12 via signal processor 34 and hearing implant 36. Specifically, when a fault is detected that requires alarming, controller 20 may send an inaudible signal to signal processor 34 associated with the alarm. As used herein, an "inaudible signal" may refer to any signal that is not itself intended to be audibly perceived by a human, and may include data signals transmitted by a wired or wireless connection.

In various respects, an inaudible signal may refer to a signal that cannot be sensed in normal usage. As described above, controller 20 may send the inaudible signal to signal processor 34 via a wired or wireless connection. In the case of a wired connection, the inaudible signal may primarily be a voltage signal. In the case of a wireless connection, the inaudible signal may be any suitable digital signal sent via any suitable wireless protocol, including but not limited to Bluetooth, Bluetooth Low Energy, WiFi, MedRadio, MICS, and/or ISM connections. In either case, the inaudible signal may be a trigger signal with components that cause signal processor 34 to respond as desired. For example, the signal may be an oscillating signal such as a sinusoidal or square wave signal, where a particular component of the signal such as the amplitude, frequency, phase, other component, or combination thereof dictates the response of the signal processor 34. For example, receipt of a signal with a particular amplitude of oscillation may trigger signal processor 34 to generate a desired alarm signal as will be described below. In some embodiments, the components of the signal may depend on the type of alarm signal as will be described in further detail below. For example, the frequency of the signal may depend on whether the alarm is associated with a hazard or advisory condition, as described in further detail below.

In response to receiving the inaudible signal associated with the alarm of the circulatory support system, signal processor 34 may generate a signal to be transmitted to the inner ear of the patient 12. Signal processor 34 may transmit the generated signal to the inner ear of the patient 12 via hearing implant 36. For example, if hearing implant 36 is implanted into the bone of the patient behind ear 2 of the patient, signal processor 34 may generate a signal of vibrations or sound waves and transmit it to the bone via implant 36. The vibrations or sound waves may then be conducted along the bone of the patient to the inner ear, so that patient 12 may audibly perceive the vibrations or sound waves. In contrast to a tone emitted by a speaker on controller 20 that may be drowned out by ambient noise and/or difficult to discern for an individual with deficiencies in their outer or middle ear, this improved alarm transmission ensures that the patient directly perceives the alarm at the inner ear of the patient. Moreover, while a tone emitted by a speaker on controller 20 may disturb others in the vicinity of the patient and draw unwanted attention to the patient, since the signals associated with the alarm are only audible at the inner ear of the patient, the alarm may remain private as may be desired by the patient.

It may be desirable for controller 20 to simultaneously transmit both the inaudible signal described above to signal processor 34, and an audible tone emitted from a speaker disposed on controller 20 or on any other patient worn components of system 10. In order to ensure appropriate alerts are received without unnecessary disturbances, in some embodiments, alarm transmission using controller 20, signal processor 34, and hearing implant 36 may be adaptable based on the type of fault detected. Depending on the seriousness of the fault detected, the audible tone emitted from a speaker on the controller 20 may be muted or mutable by the patient. For example, if the fault detected is associated with one of the advisory alarms described above, the audible tone may be automatically muted, mutable by the patient via an input on the controller, or not emitted at all by controller 20 or speaker thereof. On the other hand, if the fault detected is associated with one of the hazard alarms described above, the audible tone may not be muted or mutable by the patient, and it may persist until the fault is attended to and/or resolved. In this way, it is ensured that the patient, medical caregiver, or other individual in the vicinity may be adequately alerted to attend to the faults, and only the most serious faults may disturb anyone other than the patient.

In many embodiments, signal processor 34 may also emit an audible tone in addition to transmitting an alarm signal directly to the inner ear as described above. For example, signal processor 34 may generate both an audible tone to be output by a speaker disposed on signal processor 34 and a signal to be conducted by the bone implant to the inner ear of the patient. In some embodiments, audible tones may be emitted by signal processor for any type of alarm. In other embodiments, the audible tone emitted by signal processor 34 may be limited to apply during a hazard alarm. For example, if controller 20 detects a hazard alarm, the inaudible signal transmitted to signal processor 34 may trigger the signal processor 34 to emit both the audible tone and the bone conduction signal. If controller 20 only detects an advisory alarm, the inaudible signal transmitted to signal processor 34 may only trigger the signal processor 34 to emit the bone conduction signal. As with the audible tones emitted by controller 20 described above, the audible tone emitted by signal processor 34 may be mutable by the patient depending on the type of alarm. For example, if there is an advisory alarm, the patient may mute the audible tone emitted by signal processor 34 by an input coupled to signal processer 34, such as a button. If there is a hazard alarm, the patient may not mute the audible tone emitted by signal processor 34, and it may persist until the fault is attended to and/or resolved.

In order to conserve battery 342 and prolong the usage of signal processor 34, it may be desirable to keep signal processor 34 powered off or in a low power mode when not receiving or transmitting signals. Accordingly, signal processor 34 and its components may generally be powered off or in a low power mode by default, but may be configured to be activated so as to be powered on in response to a signal received from controller 20. In some embodiments, signal processor 34 may include an a secondary radio or other receiver that does not require power from battery 342 that is configured to receive a wake up signal from controller 20. For example, the wake up signal may include an RFID tag that may be configured to activate one or more components of signal processor 34. The wake up signal may be sent to signal processor 34 by controller 20 when a fault is detected, prior to transmission of the inaudible alarm signals described herein. In response to the wake up signal received from controller 20, the secondary radio or other receiver may be configured to power on signal processor 34 so that subsequent signals may be received from controller 20 and processing and transmission of alarm signals as described above may be carried on. Upon waking up, signal processor 34 may transmit a confirmation signal to controller 20 to initiate alarming. In addition to sending the wake up signal to signal processor 34, in some embodiments, it may also be desirable in some cases to send the wake up signal to a caregiver. For example, the wake up signal may be simultaneously transmitted to another device that alerts the caregiver of the alarm and/or makes a record of the alarm for the caregiver's attention. It will be understood that this additional transmission of the wake up signal may only be done for hazard alarms.

Figure 4A:
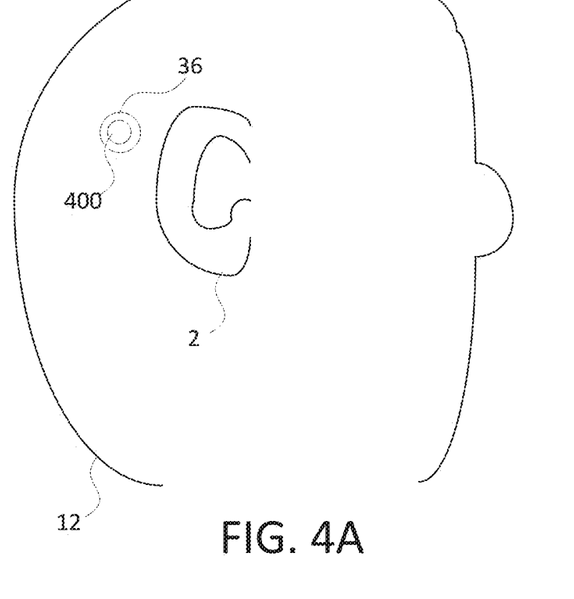
FIG. 4A is an illustration of a bone conduction implant, in accordance with many embodiments.
Figure 4B:
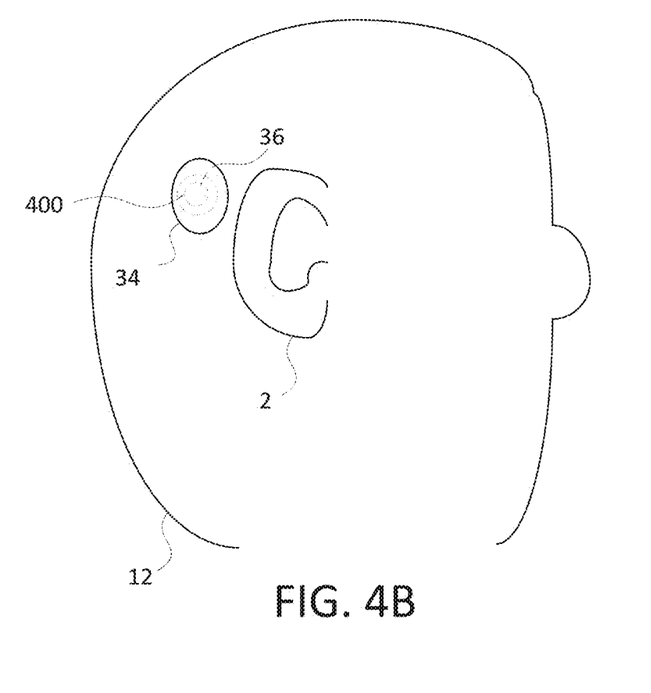
FIG. 4B is an illustration of a sound processor coupled to the bone conduction implant shown in FIG. 4A, in accordance with many embodiments.
Figure 5:
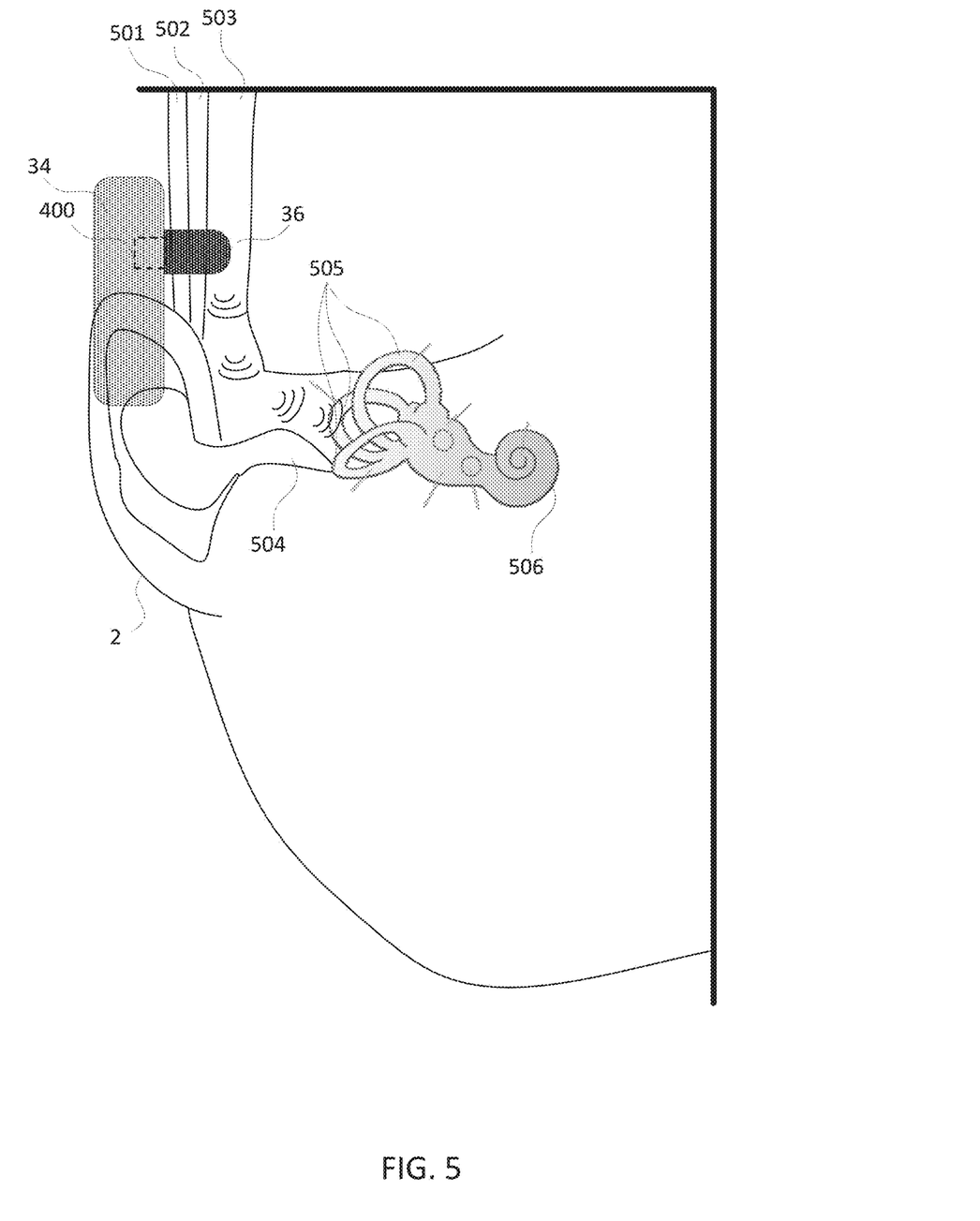
FIG. 5 is an illustration of a bone conduction implant and sound processor transmitting an alarm to the inner ear of a patient, in accordance with many embodiments.

FIG. 4A is an illustration of a bone conduction implant, and FIG. 4B is an illustration of a sound processor coupled to the bone conduction implant shown in FIG. 4A, in accordance with many embodiments. As can be seen in FIG. 4A, in some embodiments, hearing implant 34 may be a bone conduction implant anchored in bone behind the ear 2 of a patient 12. As can be seen with further reference to FIG. 5, bone conduction implant 34 may be implanted through the skin 501, periosteum 502, and into the skull bone 503 of the patient 12. Bone conduction implant 34 may include an abutment 400 that extends outside of the skin 501 of the patient 12 such that it is exposed when bone conduction implant 36 is implanted into the skull bone 503 of patient 12. As described above, signal processor 34 may be coupled to bone conduction implant 34. As can be seen in FIGS. 4A, 4B, and 5, signal processor 34 may be coupled to abutment 400. In some embodiments, signal processor 34 may be releasably coupled to abutment 400. For example, a patient 12 may snap on and snap off signal processor 34 from abutment 400 in order to charge signal processor 34, replace the batteries of signal processor 34, or otherwise replace signal processor 34 itself with another signal processor similarly configured.

As can be seen with reference to FIG. 5, when signal processor 34 is coupled to bone conduction implant 36, it may be configured to transmit vibrations or sound waves generated by signal processor 34 to be conducted along skull bone 503 to be received by auditory portions 505 (such as the canals) of the patient's cochlea 506. The patient may then audibly perceive the vibrations or sound waves generated by signal processor 34. By conducting the vibrations or sound waves along skull bone 503, the patient's ear canal 504 may be bypassed, which may be beneficial in cases where the patient is in a loud environment or the patient has problems in its outer or middle ear. Although described herein as implanted and extending through layers 501, 502, and 503 and directly receiving vibrations or sound waves from signal processor 34, it will be understood that bone conduction implant 36 may also be implanted so that it lies in skull bone 503 and is remotely coupled to signal processor 34. For example, bone conduction implant 36 may be wirelessly coupled to signal processor 34. Additionally, in some embodiments, bone conduction implant 36 may be implanted in a tooth of patient 12. For example, bone conduction implant 36 may wirelessly receive signals from signal processor 34 and transmit signals based on the signals received from the tooth to the skull bone so that the alarm is audibly perceived by the patient.

Figure 6:
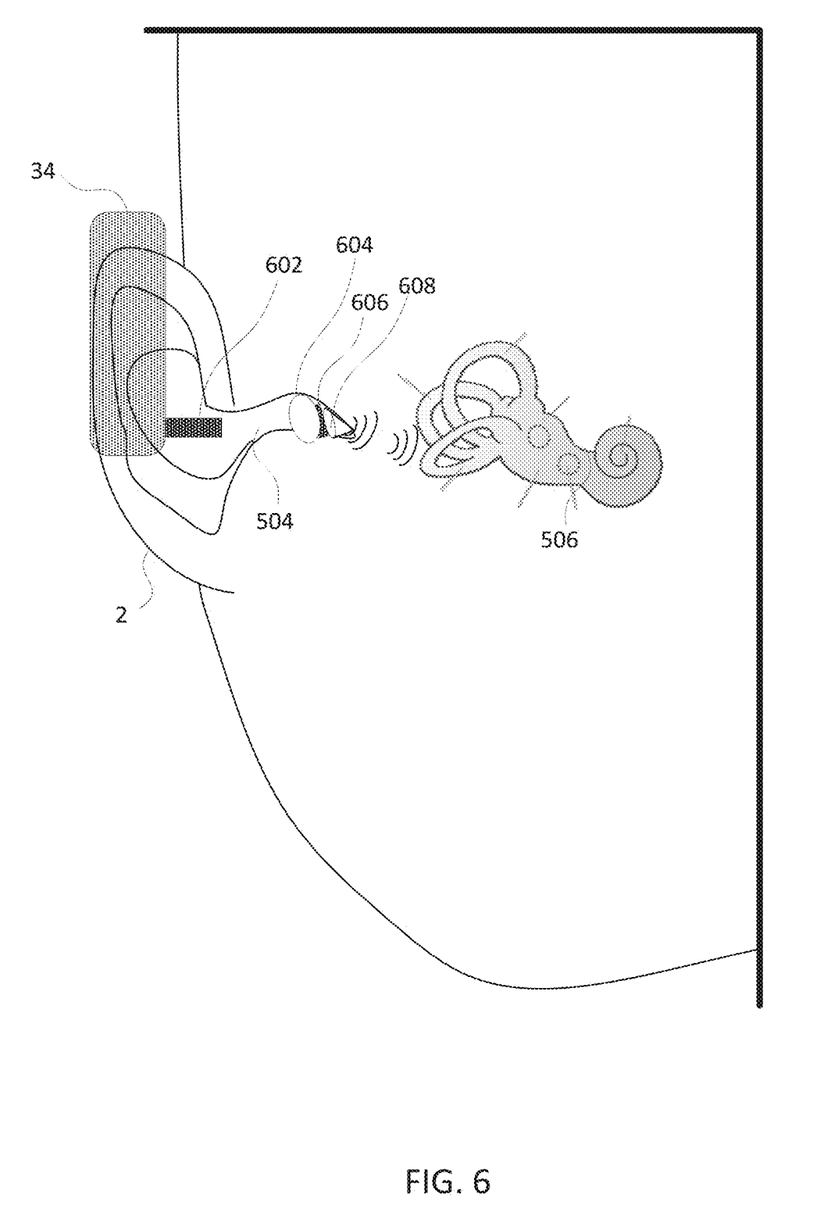
FIG. 6 is an illustration of a hearing implant and photon processor transmitting an alarm to the inner ear of a patient, in accordance with many embodiments.

FIG. 6 is an illustration of a hearing implant and photon processor transmitting an alarm to the inner ear of a patient, in accordance with many embodiments. In the embodiment shown in FIG. 6, a signal processor 34 may include or be coupled to a photon processor 602. As opposed to conducting a sound wave or vibration along the skull bone of a patient as described above with respect to FIG. 5, photon processor 602 may be configured to transmit a photonic signal to a lens 604 resting on the eardrum 608 of the patient. For example, photon processor 602 may be configured to generate a light signal that corresponds to an alarm signal received from controller 20 by signal processor 34. The lens 604 may be coupled to an actuator 606 that is configured to generate vibrations or sound waves based on the photonic signal received from processor 602 by the lens 604. These vibrations or sound waves generated by actuator 606 may then be conducted from the eardrum of the patient to the inner ear of the patient 506. As with the example described in FIG. 5, it will be understood that transmission of a photonic signal that is converted to vibrations or sound waves directly at the eardrum 608 of a patient may improve the ability of a patient to discern an alarm.

Figure 7:
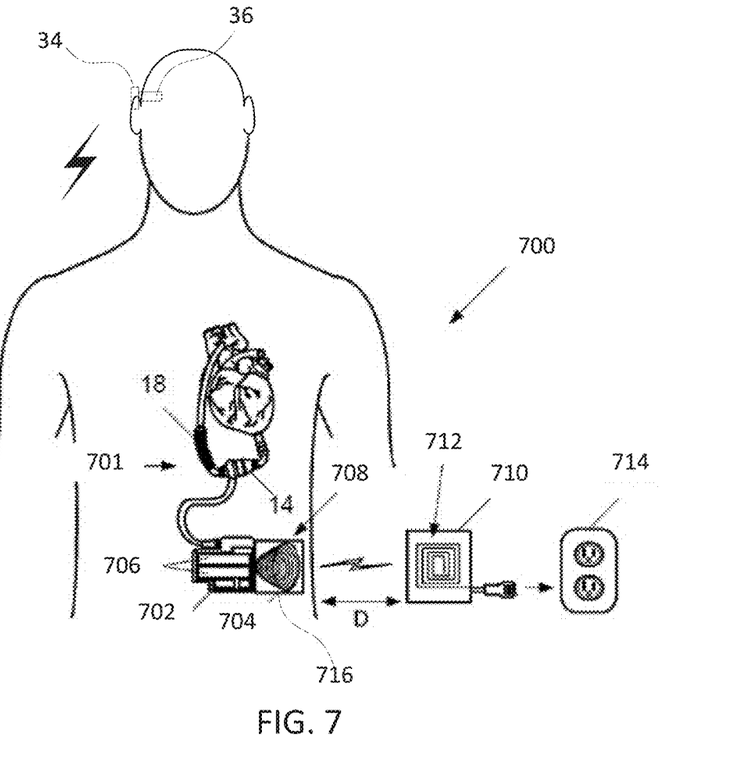
FIG. 7 is an illustration of a mechanical circulatory support system implanted in a patient's body, in accordance with many embodiments.

FIG. 7 is an illustration of a mechanical circulatory support system implanted in a patient's body, in accordance with many embodiments.

Although the systems described above have primarily been directed to systems with external controllers, similar systems and approaches can be applied to systems with implantable controllers. FIG. 7 illustrates an exemplary embodiment of a mechanical circulatory support system 700 with a transcutaneous energy transfer system (TETS) and associated controller implanted in a patient's body. System 700 includes internal components 701 including a cannula 18, a blood pump 14, a rechargeable power storage device 702, also referred to herein as an implantable power supply 702, and a power receiving unit 704. The power receiving unit 704 includes a TETS receiver 708 that can be, for example, a receiver, a resonator, and inductive coil or the like, that can be coupled to the power storage device 702, which is the electrical load of the power receiver unit 704. The mechanical circulatory support system 700 also includes a power transmitter unit 710, that is external to the patient. The transmitter unit 710 includes a transmitter resonator 712, also referred to herein as a TETS transmitter 712. The transmitter resonator 712 can include, for example, a coil, including an inductive coil that is configured to be coupled to an electric power source 714 such as an electrical wall outlet or external power sources. When the transmitter unit 710 is powered by, for example, connection to the electric power source 714, an electrical current is generated in the coil of the transmitter resonator 712.

When the receiver unit 704 in the patient comes within a separation distance D of the transmitter unit 710, the mechanical circulatory support system 700 is able to wirelessly transfer energy from the transmitter unit 710 to the receiver unit 704 to recharge the power storage device 702 of the internal components 701. In one embodiment, at a given separation distance D being in the range of 2.5 cm to 35 cm, the transmitter unit 710 is able to deliver power in the range of 5 W to 20 W to the receiver unit 704 to recharge the batteries 706 in the power storage device 702 of the internal components 701.

Power receiver unit 704 may also include a controller 716 that performs control, detects faults, transmits alarms, and performs other functions of system 700 as described above with respect to controller 20. Since the controller 716 may be implanted within the body of the patient, wireless communication with a signal processor 34 may be required. Moreover, since the wireless communication must occur through the body of the patient, communication with signal processor 34 may require a stronger wireless signal. For this reason, controller 20 may be configured to communicate using signals and/or frequencies used for diagnostic and therapeutic purposes in implanted medical devices. For example, controller 20 may be configured to communicate using frequencies in the Medical Device Radiocommunication Service (MedRadio) and/or Medical Implant Communication Service (MICS) spectrums. Controller 716, signal processor 34 and hearing implant 36 may otherwise operate as described above with respect to controller 20 and signal processor 34 and hearing implant 36.

Figure 8:
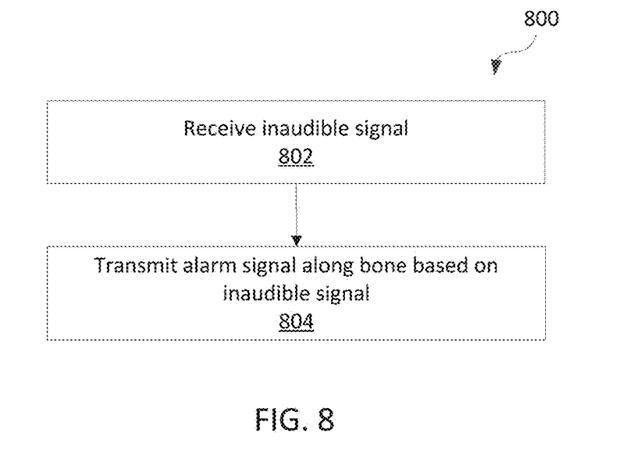
FIG. 8 is a flowchart illustrating a method of transmitting an alarm for a circulatory support system of a patient, in accordance with many embodiments.

FIG. 8 is a flowchart illustrating a method 800 of transmitting an alarm for a circulatory support system of a patient, in accordance with many embodiments. It will be understood by those skilled in the art that the order of the steps may be switched, some of the steps may be combined, and/or some of the steps may be optional. The flowchart of FIG. 8 is one example of the method and is not intended to be limiting. Thus, it will be understood by those skilled in the art that various other operation(s) disclosed in this application may be used instead of those shown in FIG. 8. Method 800 may be performed by any or all of the systems and components described above. For example, method 800 may be performed by system 10, including controller 20, any of signal processors 34, hearing implants 36, associated components thereof and/or any suitable combination thereof. As another example, method 800 may be performed by system 700, including controller 716, any of signal processors 34, hearing implants 36, associated components thereof, and/or any suitable combination thereof. The steps of method 800 will now be described with reference to FIG. 8.

At step 802, an inaudible signal associated with an alarm of a circulatory support system may be received from the circulatory support system. In some embodiments, the inaudible signal may be received from a circulatory support system by any of the signal processors 34 described herein. For example, the inaudible signal may be received from a controller of the circulatory support system, which may be an implantable controller such as controller 716 or an external controller such as controller 20. As described above, the inaudible signal may be associated with either an advisory alarm of the circulatory support system or a hazard alarm of the circulatory support system. In some embodiments, the inaudible signal may be received via a hardwired connection with circulatory support system. In other embodiments, the inaudible signal may be received by a wireless connection with circulatory support system. In some embodiments, as described above, prior to receiving the inaudible signal associated with the alarm at step 802, signal processor 34 may receive a wake up signal from the circulatory support system.

At step 804, an alarm signal may be transmitted along the bone of a patient based on the inaudible signal. In some embodiments, the alarm signal may be generated by any of signal processors 34 described herein in response to receiving the inaudible signal associated with the alarm. For example, a sound processor 34 as described herein may generate vibrations or sound waves based on the inaudible signal received at step 802 to be transmitted along the bone of a patient. The vibrations or sound waves generated by sound processor 34 may be transmitted along the bone of a patient to an inner ear of the patient such that the alarm signal is only audibly perceived by the patient. As another example, a photon processor 602 as described herein may generate light signals based on the inaudible signal received at step 802 and transmit the light signals to a lens 604 as described above, which may in turn cause actuator 606 to generate vibrations or sound waves to be transmitted to the inner ear via eardrum 608. In some embodiments, parameters of the alarm signal such as the frequency, intensity, or duration of the alarm signal may be determined based on the type of alarm associated with the first inaudible signal. For example, a hazard alarm may have a particular frequency, intensity, or duration that is different from an advisory alarm, and different hazard alarms and advisory alarms may have different frequencies, intensities, or durations. For example, a hazard alarm may have increased frequency, intensity, and/or duration as compared to an advisory alarm.

Figure 9:
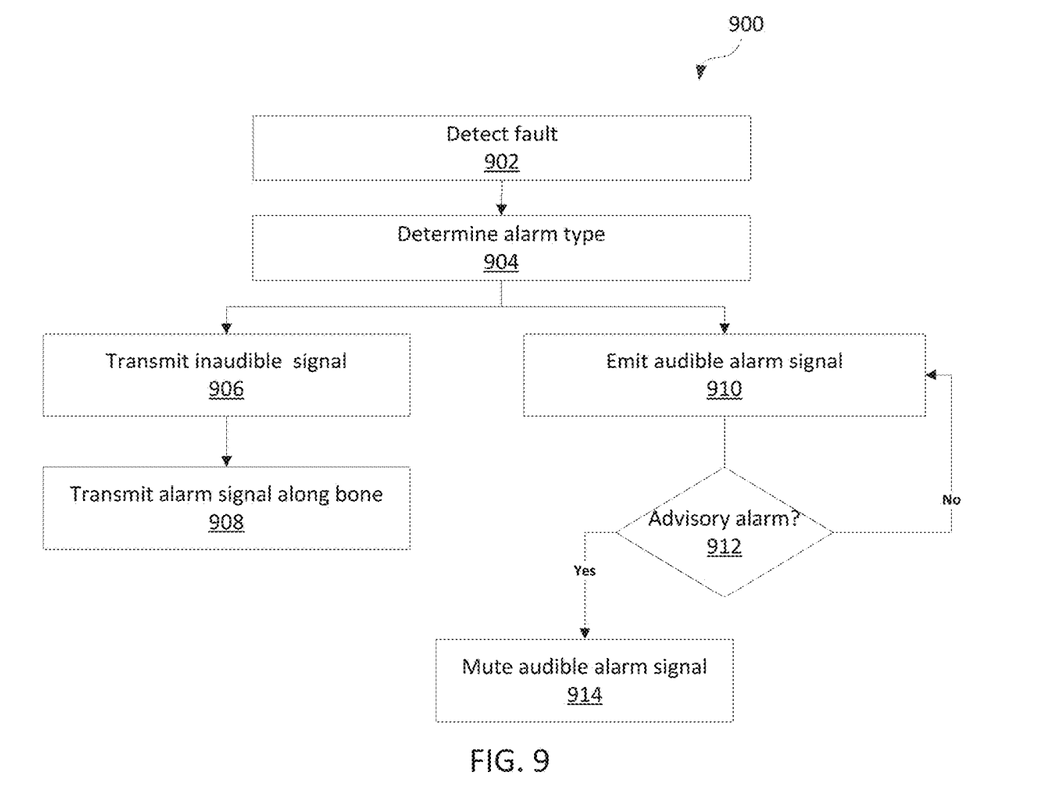
FIG. 9 is a flowchart illustrating a method of transmitting an alarm for a circulatory support system of a patient, in accordance with many embodiments.

FIG. 9 is a flowchart illustrating a method 900 of transmitting an alarm for a circulatory support system of a patient, in accordance with many embodiments. It will be understood by those skilled in the art that the order of the steps may be switched, some of the steps may be combined, and/or some of the steps may be optional. The flowchart of FIG. 9 is one example of the method and is not intended to be limiting. Thus, it will be understood by those skilled in the art that various other operation(s) disclosed in this application may be used instead of those shown in FIG. 9. Method 900 may be performed by any or all of the systems and components described above. For example, method 900 may be performed by system 10, including controller 20, any of signal processors 34, hearing implants 36, associated components thereof and/or any suitable combination thereof. As another example, method 900 may be performed by system 700, including controller 716, any of signal processors 34, hearing implants 36, associated components thereof, and/or any suitable combination thereof. The steps of method 900 will now be described with reference to FIG. 9.

At step 902, a fault may be detected. In some embodiments a controller and/or monitor of a circulatory support system may detect a fault of the circulatory support system. For example, controllers 20 or 716 may detect faults of circulatory support systems 10 or 700. The faults detected may include faults associated with cables, power sources, speeds, controllers, or other aspects of the circulatory support system, and/or any combination thereof.

At step 904, the type of alarm to be output may be determined. In some embodiments, controller 20 or controller 716 may determine the type of alarm. For example, the type of alarm may be an advisory alarm. As another example, the type of alarm may be a hazard alarm. In some embodiments, the type of alarm may be determined based on the fault or faults detected at step 902. For example, it may be determined that an advisory alarm is needed if the fault detected is a disconnected power cable, a low voltage of a power source of the circulatory support system, a low speed of the circulatory support system, a fault of a controller of the circulatory support system, or a fault of a backup power source of the circulatory support system. As another example, it may be determined that a hazard alarm is needed if the fault detected is a stopped circulatory support system, a disconnected driveline of the circulatory support system, multiple disconnected power cables, an excessively low speed of the circulatory support system, or an excessively low voltage of the power source of the circulatory support system.

At step 906, an inaudible signal may be transmitted by the controller to any of signal processors 34, and at step 908, any of signal processors 34 may transmit an alarm signal along the bone based on the inaudible signal. Steps 906 and 908 may generally occur as described above with respect to steps 802 and 804 of method 800 in accordance with many embodiments. However, in addition to transmitting inaudible signals, it can be seen that at step 910, audible alarm signals may also be emitted. In some embodiments, audible alarm signals may be emitted by controller 20 via speakers coupled thereto or disposed thereon. In other embodiments, audible alarm signals may be emitted by signal processors via speakers coupled thereto or disposed thereon.

At step 912 controller may recall whether the type of alarm determined in 904 was an advisory alarm. If it is not an advisory alarm, controller 20 may continue to emit the audible alarm signal until the alarm is attended to or otherwise resolved. If it is an advisory alarm, controller 20 may proceed to step 914, where the audible alarm signal may be muted. As described above, in some embodiments, the audible alarm may automatically be muted by controller 20 if it is an advisory alarm. In some embodiments, the alarm may be mutable by the patient or caregiver if it is an advisory alarm.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of transmitting an alarm for a circulatory support system of a patient, the method comprising:
   receiving a first inaudible signal from the circulatory support system of the patient with a sound processor that is operatively coupled to an implant anchored in a bone behind an ear of the patient, the first inaudible signal associated with an alarm of the circulatory support system;
   transmitting a second alarm signal along the bone of the patient to an inner ear of the patient based on the first inaudible signal such that the second alarm signal is audibly perceived by the patient; and
   transmitting a third signal associated with the alarm based on the first inaudible signal, wherein the third signal is an audible signal.

2. The method of claim 1, further comprising, prior to receiving the first inaudible signal, receiving a wake up signal from a controller coupled to the circulatory support system.

3. The method of claim 1, wherein transmitting the second alarm signal comprises transmitting vibrations or sound waves that are conducted along the bone of the patient such that the vibrations or sound waves are only audibly perceived by the patient when conducted along the bone of the patient.

4. The method of claim 1, wherein transmitting the second alarm signal comprises generating vibrations or sound waves that are conducted along the bone of the patient to an auditory portion of a cochlea of the inner ear of the patient.

5. The method of claim 1, wherein the first inaudible signal is associated with an advisory alarm or a hazard alarm of the circulatory support system, wherein the advisory alarm is associated with at least one of a disconnected power cable, a low voltage of a power source of the circulatory support system, a low speed of the circulatory support system, a fault of a controller of the circulatory support system, or a fault of a backup power source of the circulatory support system and the hazard alarm is associated with at least one of a stopped circulatory support system, a disconnected driveline of the circulatory support system, multiple disconnected power cables, an excessively low speed of the circulatory support system, or an excessively low voltage of the power source of the circulatory support system.

6. The method of claim 5, further comprising processing the first inaudible signal to determine if the second alarm signal should be transmitted, wherein the second alarm signal is transmitted only when the first inaudible signal is associated with the hazard alarm of the circulatory support system.

7. The method of claim 5, wherein at least one parameter of the second alarm signal is determined based on whether the first inaudible signal is associated with the advisory alarm or the hazard alarm.

8. The method of claim 7, wherein the at least one parameter comprises at least one of a frequency, intensity, or duration of the second alarm signal.

9. The method of claim 1, wherein the implant is anchored in the bone behind the ear to expose an abutment of the implant, the abutment being configured to facilitate releasable coupling of the sound processor to the implant.

10. The method of claim 1, wherein the circulatory support system comprises an implantable blood pump and an external controller communicatively coupled to the implantable blood pump, wherein receiving the first inaudible signal comprises receiving the first inaudible signal from the external controller with the sound processor from outside a body of the patient.

11. The method of claim 1, wherein the circulatory support system comprises an implantable blood pump and an implantable controller communicatively coupled to the implantable blood pump, wherein receiving the first inaudible signal comprises receiving the first inaudible signal from the implantable controller with the sound processor from within a body of the patient.

12. The method of claim 1, wherein the circulatory support system comprises an implantable blood pump and a controller communicatively coupled to the implantable blood pump, wherein receiving the first inaudible signal comprises wirelessly receiving the first inaudible signal from the controller with the sound processor.

13. The method of claim 1, wherein the circulatory support system comprises an implantable blood pump and a controller communicatively coupled to the implantable blood pump, wherein receiving the first inaudible signal comprises receiving the first inaudible signal from the controller with the sound processor via a hard wired connection between the controller and the sound processor.

14. The method of claim 1, wherein the first inaudible signal is received by the sound processor from a controller of the circulatory support system, the controller being configured to emit an audible signal associated with the alarm of the circulatory support system simultaneously with a transmission of the first inaudible signal to the sound processor.

15. A method of transmitting an alarm for a circulatory support system of a patient to a hearing implant anchored behind an ear of the patient, the method comprising:
receiving a first inaudible signal from the circulatory support system of the patient with a signal processor that is operatively coupled to the hearing implant anchored behind the ear of the patient, the first inaudible signal associated with an alarm of the circulatory support system;
transmitting a second alarm signal to an inner ear of the patient based on the first inaudible signal such that the second alarm signal is audibly perceived by the patient and transmitting a third signal associated with the alarm based on the first inaudible signal, wherein the third signal is an audible signal.

16. The method of claim 15, wherein transmitting the second alarm signal to the inner ear comprises generating vibrations or sound waves that are conducted from at least one of a tooth or a bone of the patient to an auditory portion of a cochlea of the inner ear of the patient.

17. The method of claim 16, wherein the signal processor comprises a photon processor, and wherein transmitting the second alarm signal to the inner ear comprises:
transmitting, with the photon processor, a photonic signal based on the first inaudible signal to a lens adapted to rest on an eardrum of the patient, and
generating, with an actuator coupled to the lens, vibrations or sound waves based on the photonic signal that are conducted from the eardrum of the patient to the inner ear of the patient.

18. A mechanical circulatory support system, comprising:
an implantable blood pump;
a controller communicatively coupled to the implantable blood pump;
a sound processor configured to receive a first inaudible signal from the controller associated with an alarm of the circulatory support system and to generate a second alarm signal based on the first inaudible signal; and
a bone conductor implant configured to be anchored into a bone behind an ear of a patient and operatively coupled to the sound processor, the bone conductor implant configured to transmit the second alarm signal along the bone of the patient to an inner ear such that the second alarm signal is audibly perceived by the patient;
wherein the sound processor or the controller is configured to transmit a third signal associated with the alarm based on the first inaudible signal, wherein the third signal is an audible signal.

19. The system of claim 18, wherein the sound processor is configured to wirelessly receive the first inaudible signal from the controller.

20. The system of claim 18, wherein the controller is configured to emit an audible signal associated with the alarm of the circulatory support system simultaneously with a transmission of the first inaudible signal to the sound processor.

21. The system of claim 20, wherein the audible signal emitted from the controller is configured to be mutable based on a type of the alarm.

22. The system of claim 21, wherein the audible signal emitted from the controller is configured to be mutable when the type of the alarm is an advisory alarm, wherein the advisory alarm comprises at least one of a disconnected power cable, a low voltage of a power source of the circulatory support system, a low speed of the circulatory support system, a fault of a controller of the circulatory support system, or a fault of a backup power source of the circulatory support system.

23. The system of claim 18, wherein the controller comprises an external controller.

24. The system of claim 18, wherein the second alarm signal comprises vibrations or sound waves that are conducted along the bone such that the vibrations or sound waves are only audibly perceived by the patient when conducted along the bone of the patient.

25. The system of claim 18, wherein the sound processor is configured to transmit the third signal based on a type of the alarm.

26. The system of claim 25, wherein the sound processor is configured to transmit the third signal when the type of the alarm is a hazard alarm, wherein the hazard alarm comprises at least one of a stopped circulatory support system, a disconnected driveline of the circulatory support system, multiple disconnected power cables, an excessively low speed of the circulatory support system, or an excessively low voltage of a power source of the circulatory support system.

27. The system of claim 18, wherein the sound processor is configured to be activated upon receipt of a wake up signal from the controller prior to receiving the first inaudible signal.

28. The system of claim 18, wherein the sound processor is releasably coupled to the bone conductor implant via an exposed abutment.

29. A method of transmitting an alarm for a circulatory support system of a patient, the method comprising:
   receiving a first inaudible signal from the circulatory support system of the patient with a sound processor that is operatively coupled to an implant anchored in a bone behind an ear of the patient, the first inaudible signal associated with an alarm of the circulatory support system, the alarm being a hazard alarm or an advisory alarm;
   transmitting a second alarm signal along the bone of the patient to an inner ear of the patient based on the first inaudible signal such that the second alarm signal is audibly perceived by the patient; and
   processing the first inaudible signal to determine if the second alarm signal should be transmitted, wherein the second alarm signal is transmitted only when the first inaudible signal is associated with the hazard alarm of the circulatory support system.

30. The method of claim 29, wherein:
   the advisory alarm is associated with at least one of a disconnected power cable, a low voltage of a power source of the circulatory support system, a low speed of the circulatory support system, a fault of a controller of the circulatory support system, or a fault of a backup power source of the circulatory support system; and
   the hazard alarm is associated with at least one of a stopped circulatory support system, a disconnected driveline of the circulatory support system, multiple disconnected power cables, an excessively low speed of the circulatory support system, or an excessively low voltage of the power source of the circulatory support system.

31. A method of transmitting an alarm for a circulatory support system of a patient, the method comprising:
   receiving a first inaudible signal from the circulatory support system of the patient with a sound processor that is operatively coupled to an implant anchored in a bone behind an ear of the patient, the first inaudible signal associated with an alarm of the circulatory support system, the alarm being a hazard alarm or an advisory alarm;
   transmitting a second alarm signal along the bone of the patient to an inner ear of the patient based on the first inaudible signal such that the second alarm signal is audibly perceived by the patient, wherein at least one parameter of the second alarm signal is determined based on whether the first inaudible signal is associated with the advisory alarm or the hazard alarm.

32. The method of claim 31, wherein:
   the advisory alarm is associated with at least one of a disconnected power cable, a low voltage of a power source of the circulatory support system, a low speed of the circulatory support system, a fault of a controller of the circulatory support system, or a fault of a backup power source of the circulatory support system; and
   the hazard alarm is associated with at least one of a stopped circulatory support system, a disconnected driveline of the circulatory support system, multiple disconnected power cables, an excessively low speed of the circulatory support system, or an excessively low voltage of the power source of the circulatory support system.

33. The method of claim 31, wherein the at least one parameter comprises at least one of a frequency, intensity, or duration of the second alarm signal.

* * * * *